United States Patent [19]
Riley

[11] Patent Number: 5,882,612
[45] Date of Patent: Mar. 16, 1999

[54] THERMALLY CONDUCTIVE STERILIZATION TRAY

[75] Inventor: Edward D. Riley, Falmouth, Me.

[73] Assignee: Riley Medical, Inc., Auburn, Me.

[21] Appl. No.: 892,050

[22] Filed: Jul. 14, 1997

[51] Int. Cl.[6] .................... A61L 2/00; A61L 2/16
[52] U.S. Cl. .................. 422/300; 422/297; 206/363; 206/438; 206/439; 220/4.01; 220/677; 248/309.1; 248/346.04
[58] Field of Search ..................... 422/292, 297, 422/300, 307; 248/201, 309.1, 311.2, 346.04; 206/363, 364, 438, 439; 220/4.01, 677

[56] References Cited

U.S. PATENT DOCUMENTS

| | | | |
|---|---|---|---|
| 1,887,761 | 11/1932 | Hauser | 220/4.01 |
| 4,978,510 | 12/1990 | Smith | 422/310 |
| 5,384,103 | 1/1995 | Miller | 422/310 |
| 5,411,136 | 5/1995 | Brigham | 422/300 |
| 5,424,048 | 6/1995 | Riley | 422/300 |

*Primary Examiner*—Krisanne Thornton
*Assistant Examiner*—Fariborz Moazzam
*Attorney, Agent, or Firm*—Cesari and McKenna, LLP

[57] ABSTRACT

A sterilization tray is constructed primarily of a single stamped metal part which forms the bottom wall and at least two opposite side walls of the tray. The side walls of the tray are joined by end closures which form the end walls of the tray. In one tray embodiment, the end closures are plastic end walls which are hooked to the ends of the side walls. In a second embodiment, the end closures are formed by a bottom wall extension of the metal part which are folded up to form the tray end walls and plastic corner pieces which are hooked to the adjacent ends of the side and end walls. The tray is highly thermally conductive yet relatively inexpensive to make in quantity.

10 Claims, 5 Drawing Sheets

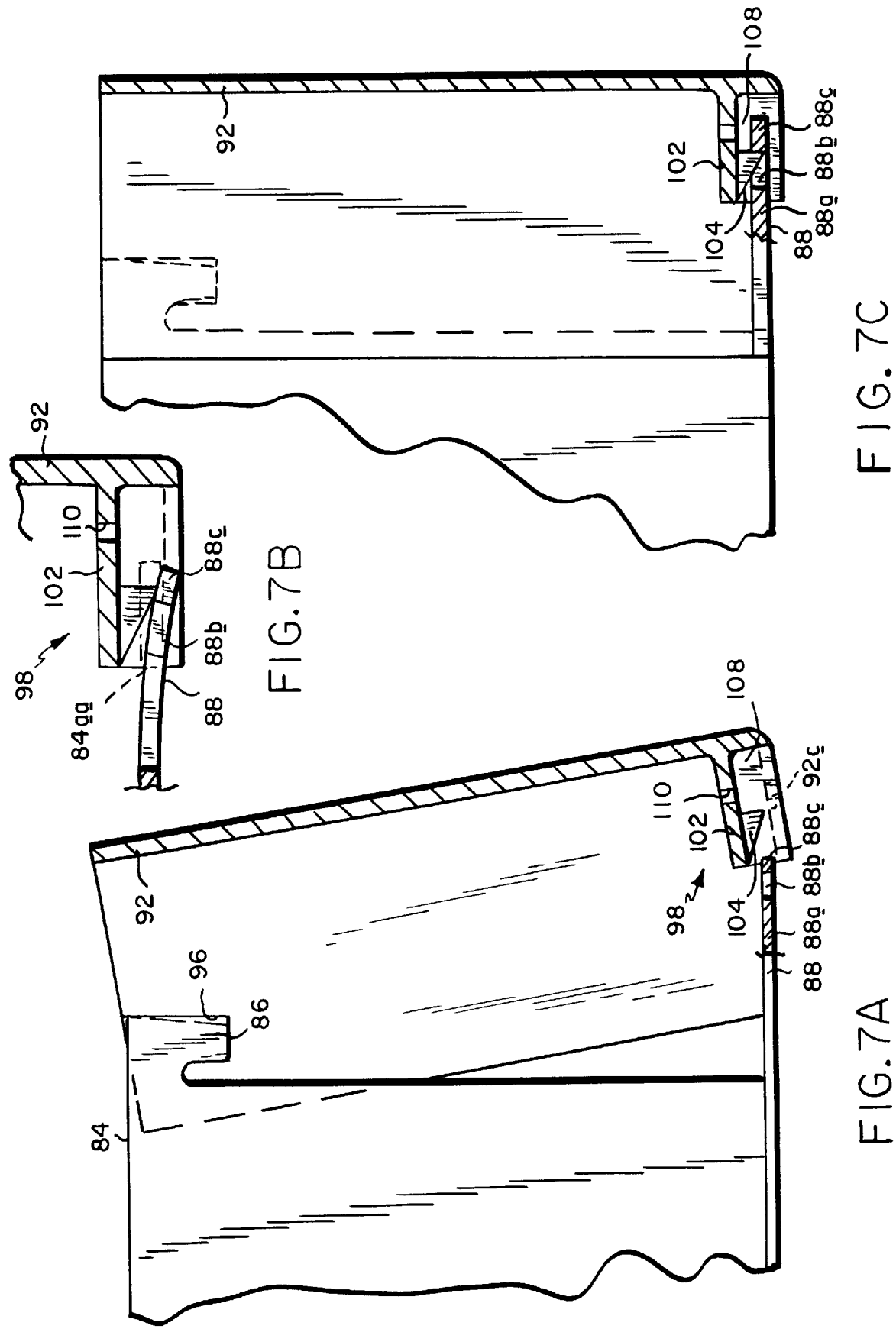

THERMALLY CONDUCTIVE STERILIZATION TRAY

This invention relates to an open top container or tray. It relates more particularly to a sterilization tray to facilitate sterilizing surgical instruments.

BACKGROUND OF THE INVENTION

Surgical instruments are often transported in a box-like tray having a bottom wall and upstanding side and end walls all of which have vent holes. Prior to use, the instruments are placed in the tray and subjected to sterilization under pressure. Following sterilization, the tray full of instruments may be transported to an operating room and placed close to the surgical team whose members may withdraw the instruments from the tray as needed for the particular surgical procedure being performed. Usually, the instruments are selectively arranged in the tray so that the instruments can be picked from the tray in the order that they are needed for the particular surgical procedure.

During sterilization a substantial amount of steam accumulates in the tray. At the end of the sterilization process as the pressure drops, this water vaporizes. The heat to vaporize the water is mainly from conduction in the tray. Also, a drying time may be included at the end of sterilization. During this time, heat radiates from the sterilizer walls to the tray and is conducted through the tray walls to vaporize any residual water in the tray. Therefore to minimize the sterilization time, it is important that the tray be thermally conductive.

For this reason, the sterilization trays have historically been made entirely of a metal such as stainless steel or aluminum. It is easy to stamp and fold sheet metal to form a tray. However, it is extremely difficult, if not impossible, to produce a tray with rounded corners in this fashion. Round corners are desirable because the trays are often wrapped in anti-microbial paper or plastic jackets and during such handling any sharp corners might tear the jackets. Trays with rounded corners can be produced by a drawing process. However, the dies for doing this are very expensive so that the unit cost of such drawn metal trays is quite high.

Because of such cost considerations, the medical products industry has in recent years resorted to making sterilization trays with rounded corners entirely out of a plastic material able to withstand the sterilization temperatures. Unfortunately however, the plastic materials used for this purpose have relatively low thermal conductivity. Therefore, the tray actually acts as a thermal barrier. As a result, it takes longer to sterilize the instruments than would be the case if the instruments were supported in a metal tray.

SUMMARY OF THE INVENTION

Accordingly, it is an object of this invention to provide a sterilization tray which is highly thermally conductive and yet can be made at relatively low cost.

Another object of the invention is to provide a tray of this type which is rugged and reliable and able to withstand sterilization temperatures.

Still another object of the invention is to provide a sterilization tray which can easily be fabricated in a variety of different sizes.

Other objects will, in part, be obvious and will, in part, appear hereinafter. The invention accordingly comprises the features of construction, combination of elements and arrangement of parts which will be exemplified in the following detailed description, and scope of the invention will be indicated in the claims.

Briefly, the sterilization tray comprises a main or major metal portion which forms the tray bottom and at least two walls of the tray and a plurality of smaller plastic pieces which connect the walls of the tray to form a box-like enclosure with rounded corners. In two embodiments of the invention, the tray includes two plastic pieces which form the tray end walls. In another tray embodiment, the tray end walls are also of metal and four plastic corner pieces are employed to connect the side and end walls of the tray. In all embodiments, the plastic pieces are secured to the metal portion of the tray using special hook and eye connections to be described in more detail later.

The main metal portion of the tray is a simple stamped metal part which can be made in quantity quite inexpensively. The smaller, plastic pieces which form the rounded corners of the tray are molded parts which are also very inexpensive to make in quantity. Also, the assembly of the plastic pieces to the metal portion of the tray can be carried out by relatively unskilled personnel without requiring any special tools or equipment. Therefore, the overall cost of the tray may be kept to a minimum. Yet, since tray is primarily made of metal, the tray is highly thermally conductive.

BRIEF DESCRIPTION OF THE DRAWINGS

For a fuller understanding of the nature and objects of the invention, reference should be had to the following detailed description taken in connection with accompanying drawings, in which:

FIGS. 7A to 7C are fragmentary sectional views of the FIG. 6 tray being assembled.

DETAILED DESCRIPTION OF THE PREFERRED EMBODIMENTS

Figure 1:
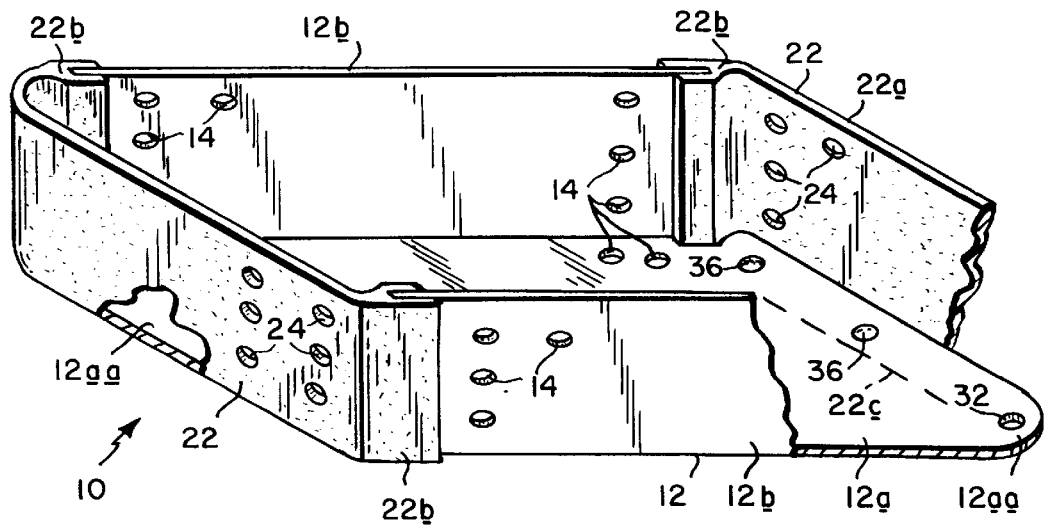
FIG. 1 is an isometric view with parts broken away showing a first sterilization tray embodiment according to the invention.
Figure 2:
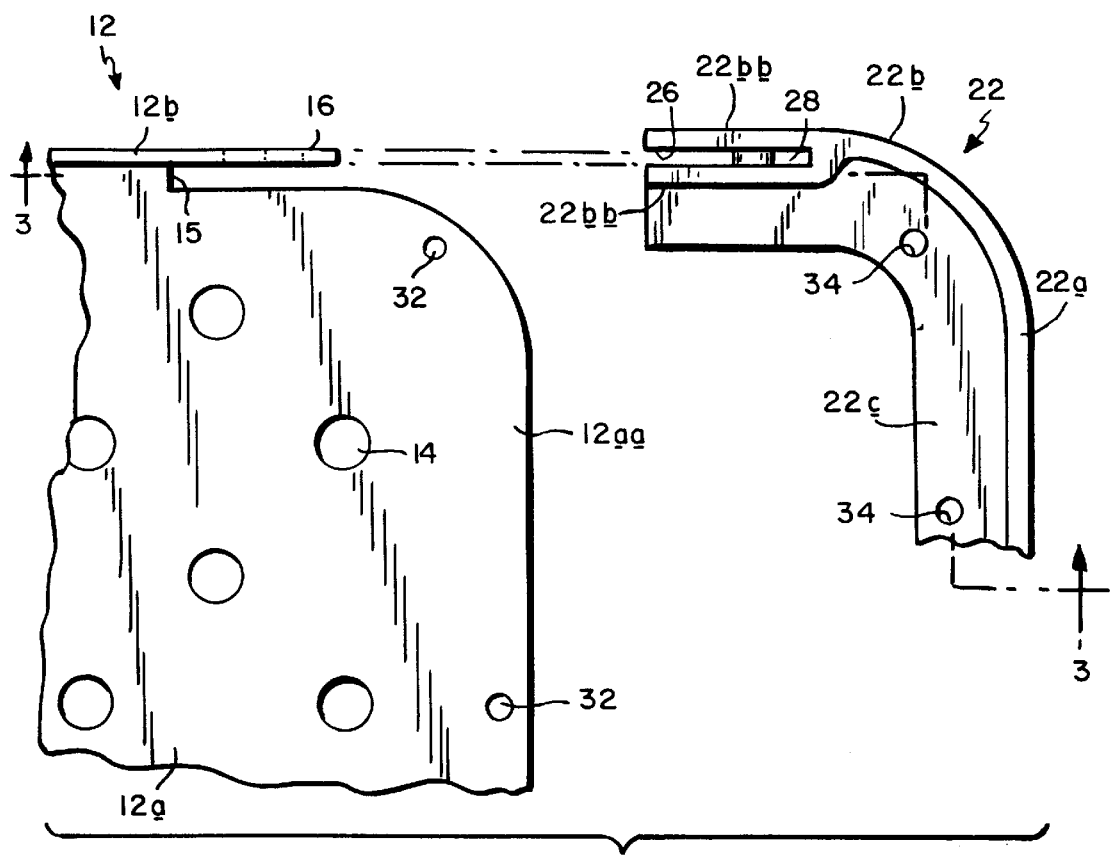
FIG. 2 is a fragmentary exploded plan view, on a larger scale, showing a corner of the FIG. 1 tray in a disassembled condition.
Figure 3:
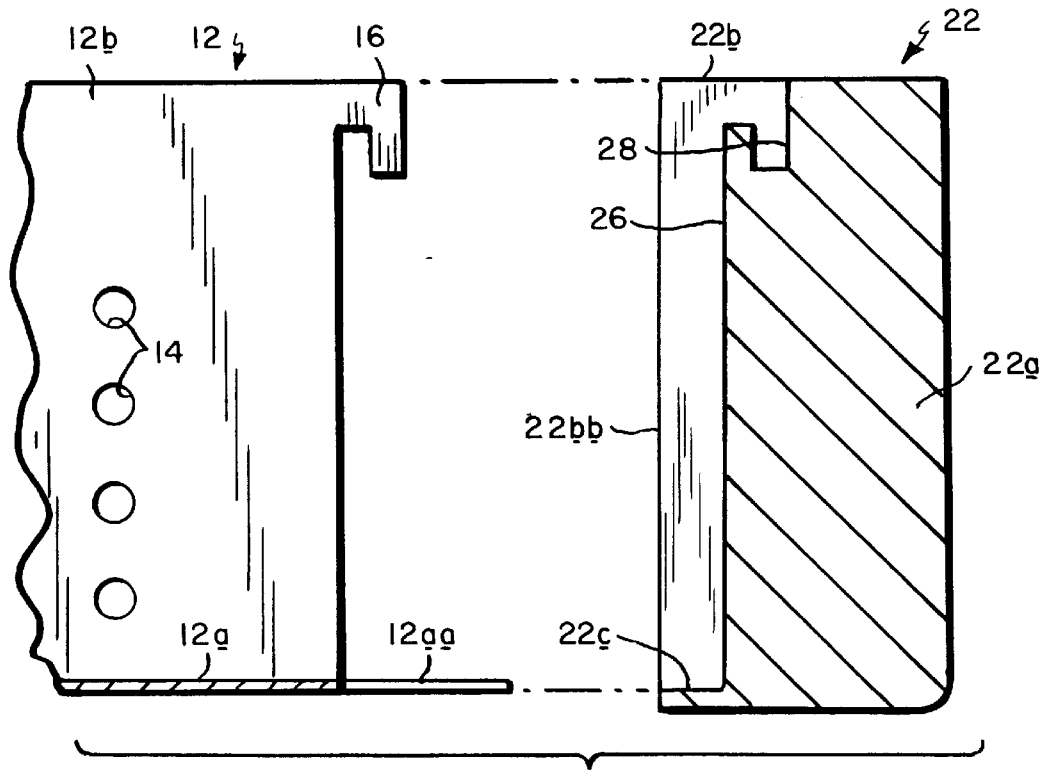
FIG. 3 is a sectional view taken along line 3—3 of FIG. 2.

Referring to FIGS. 1 to 3 of the drawings, a first embodiment of the sterilization tray is shown generally at 10. It comprises a metal tray portion 12 consisting of a generally rectangular bottom wall 12a and a pair of rectangular side walls 12b extending up from opposite edges of bottom wall 12a so as to form a channel. Preferably, a multiplicity of vent holes 14 are formed in the bottom and side walls to facilitate the circulation of steam through the tray during the sterilization process.

As best seen in FIGS. 1 and 2, a pair of mirror-image tongues 12aa are present at opposite ends of bottom wall 12a. These tongues extend beyond the corresponding ends of the side walls 12b and have rounded corners. The tongues are slightly narrower than bottom wall 12a thereby leaving gaps 15 (FIG. 2) between the side edges of each tongue and the adjacent side walls 12b.

As shown in FIGS. 2 and 3, a downwardly facing, generally L-shaped hook 16 is formed at the end of each side wall 12b at the upper edge thereof. Each hook 16 is spaced laterally from the adjacent edge of the corresponding tongue 12aa by the width of a gap 16.

The tray portion 12 may be fabricated from a single metal blank by a simple stamping and folding operation. Therefore, it can be made in quantity at relatively low cost.

Referring to FIGS. 1 to 3 of the drawings, the tray 10 also includes end closure means in the form of a pair of identical molded plastic pieces that form the end walls 22 of the tray. Each end wall has a generally flat bridging section 22a having vent holes 24 and a pair of mirror-image curved corner sections 22b at the opposite ends of section 22a. Also, an inwardly extending flange 22c extends along the bottom of each end wall 22. Flange 22c helps to rigidify the end wall and facilitates its connection to the tray portion 12 as will be described later.

As best seen in FIG. 2, the end leg or segment of each corner section 22b is thicker than the remainder of the end wall and a slot 26 extends down through that end segment. Slot 26 has an inner wall 22ba whose thickness is slightly less than the width of the gaps 16 in the tray portion 12 and an outer wall 22bb. Also, formed in the top of the corner section end segment is a generally L-shaped, downwardly facing eye or notch 28 having essentially the same dimensions and shape as the hooks 16 on tray portion 12.

End walls 22 may be of a sterilizable plastic material and can be molded in quantity at relatively low cost.

Figure 4:
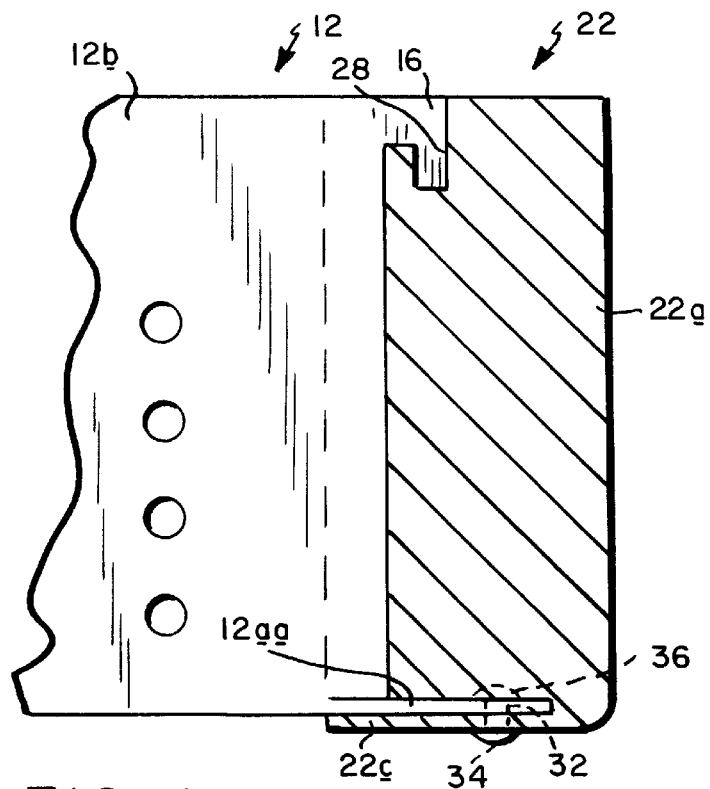
FIG. 4 is a fragmentary sectional view showing the corner connection of the FIG. 1 tray in greater detail.

As shown in FIG. 4, each end wall 22 may be attached to an end of tray portion 12 by engaging the upper edges of the end wall corner sections 22b against the ends of the tray portion walls 12b so that the hooks 16 on the latter hook into the corresponding eyes 28 of that end wall 22. Each end wall 22 is slightly taller than the side walls 12b so that the edge margin of each end wall is received in the slot 26 of the corresponding end wall corner section 22b and so that the end wall flange 22c engages under the corresponding tongue 12aa of tray portion 12. The corner curvatures of the end walls 22 and tongues 12aa correspond so that when the end walls are assembled to tray portion 12 as shown in FIG. 4, there are essentially no gap between the tongues 12aa and the end walls 22.

Preferably, each end wall 22 is permanently secured to tray portion 12. For this, a plurality of holes 32 may be provided in each tongue 12aa adjacent the edge thereof Similar holes 34 may be formed in the end wall flange 22c. When the end wall is assembled to tray portion 12 as illustrated in FIG. 4, the holes 32 and 34 are in register so that they can accept a rivet 36 or similar fastener which positively fixes the lower edge of each end wall 22 to the tray portion 12.

When tray 10 is fully assembled as shown in FIG. 1, it constitutes a relatively low cost, rigid, rugged, box-like structure which is, for the most part, highly thermally conductive so that during the sterilization process, the tray contents can be sterilized and dried in a minimum amount of time.

Figure 5:
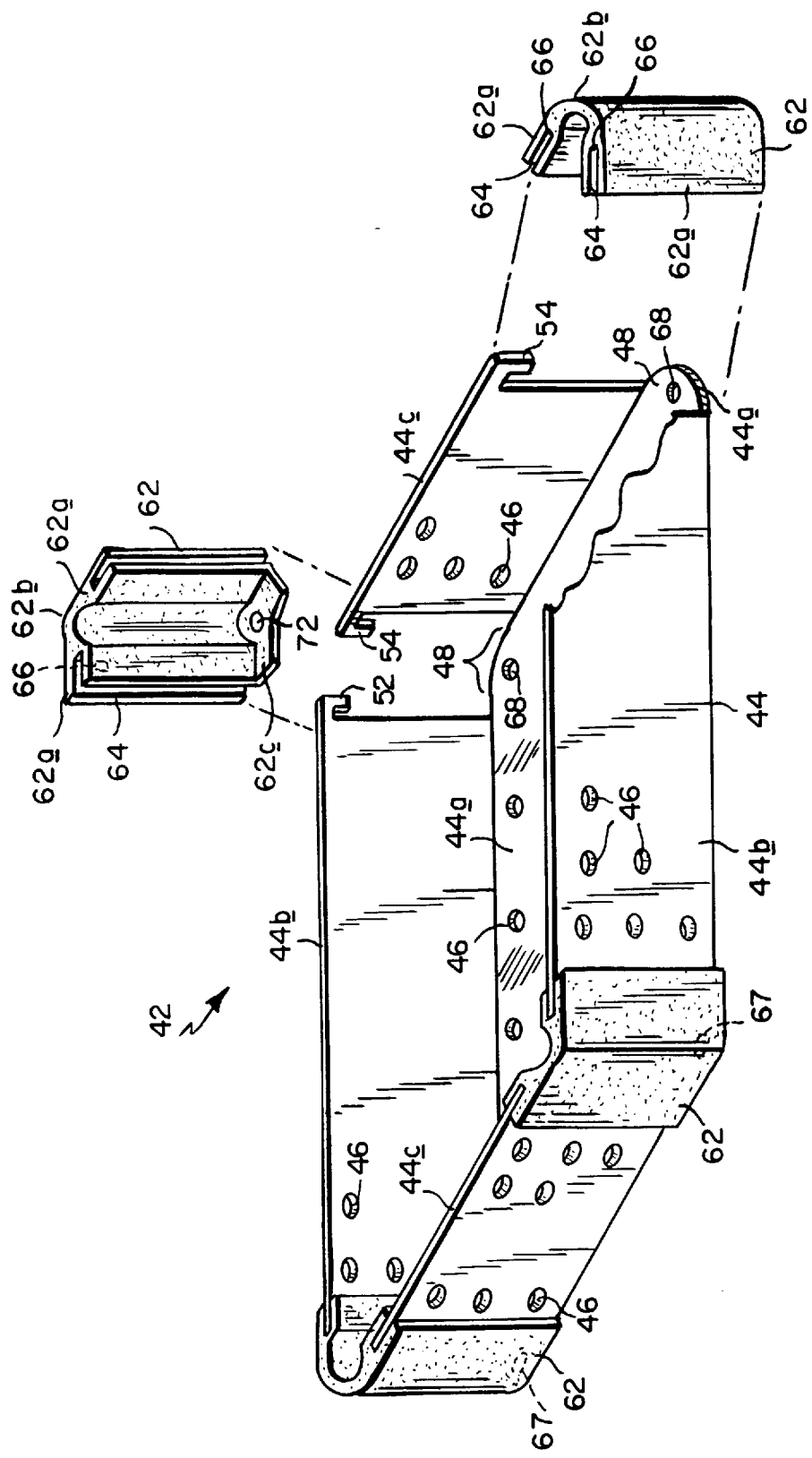
FIG. 5 is an exploded perspective view, with parts broken away, of a second embodiment of the sterilization tray.

Sterilization trays 10 of different width obviously require end walls 22 having corresponding different lengths. To avoid that requirement and to further minimize costs, the metallic main tray portion may be designed to include end walls as well as side walls. FIG. 5 illustrates a sterilization tray 42 of this type.

Tray 42 includes a metallic main portion 44 consisting of a rectangular bottom wall 44a, a pair of upstanding rectangular side walls 44b and a pair of rectangular end walls 44c all stamped and formed from a single metal blank. In this embodiment, the end walls 44c form part of the tray's end closure means. As with the FIG. 1 tray, the main portion 44 may be provided with a multiplicity of vent holes 46.

The side and end walls of tray portion 44 are spaced apart on bottom wall 44a so as to leave gaps 48 at the corners of portion 44 where the corners of bottom wall 44a are rounded. Also, hooks 52 similar to hooks 16 described above are provided at the opposite ends of side walls 44b at the upper edges thereof. Similar hooks 54 are also present at the opposite ends of end walls 44c.

The corner gaps 48 of tray portion 44 are closed by a plurality, herein four, of identical molded plastic corner sections 62 which constitute the rest of the end closure means. Each corner section 62 has a pair of orthogonal relatively thick segments or legs 62a, 62a connected by a thinner web 62b. Each end segment is provided with a vertical slot 64 similar to slots 26 in the end walls 22. An L-shaped notch or eye 66 is provided at the top of each segment 62a, 62a to receive the hooks 52 or 54 of the tray portion 44.

Also, each corner section 62 includes an inwardly extending bottom flange 62c which is similar to, and performs the same function as, the flange 22c in the FIG. 1 tray.

Each corner section 62 is connected to the tray portion 44 in more or less the same way as each end wall 22 is connected to tray portion 12 of tray 10. More particularly, the upper end of each corner section 62 is positioned at a corner of tray portion 44 so that a side wall hook 52 hooks into the eye 66 at one segment 62a of the corner section 62 and the end wall hook 54 hooks into the eye 66 at the other segment 62a of that section. Then, the lower end of the corner section is swung against the rounded corner of the bottom wall 44a so that the adjacent edge margins of the side and end walls are received in the corner section slots 64 and so that flange 62c underlies that corner of bottom wall 44a. The lower end of the corner section may be fixed to tray portion 44 by inserting a rivet 67 through registering holes 68 and 72 in the corner of bottom wall 44a and the flange 62c, respectively.

When assembled, the tray 42 has all of the advantages of tray 10. In addition, it has more thermally conductive surface area. Moreover, the same corner section 62 can be used to form trays having a variety of different length and width dimensions so long as the dimensions of the gaps 48 in the main tray portion 44 remain the same.

Figure 6:
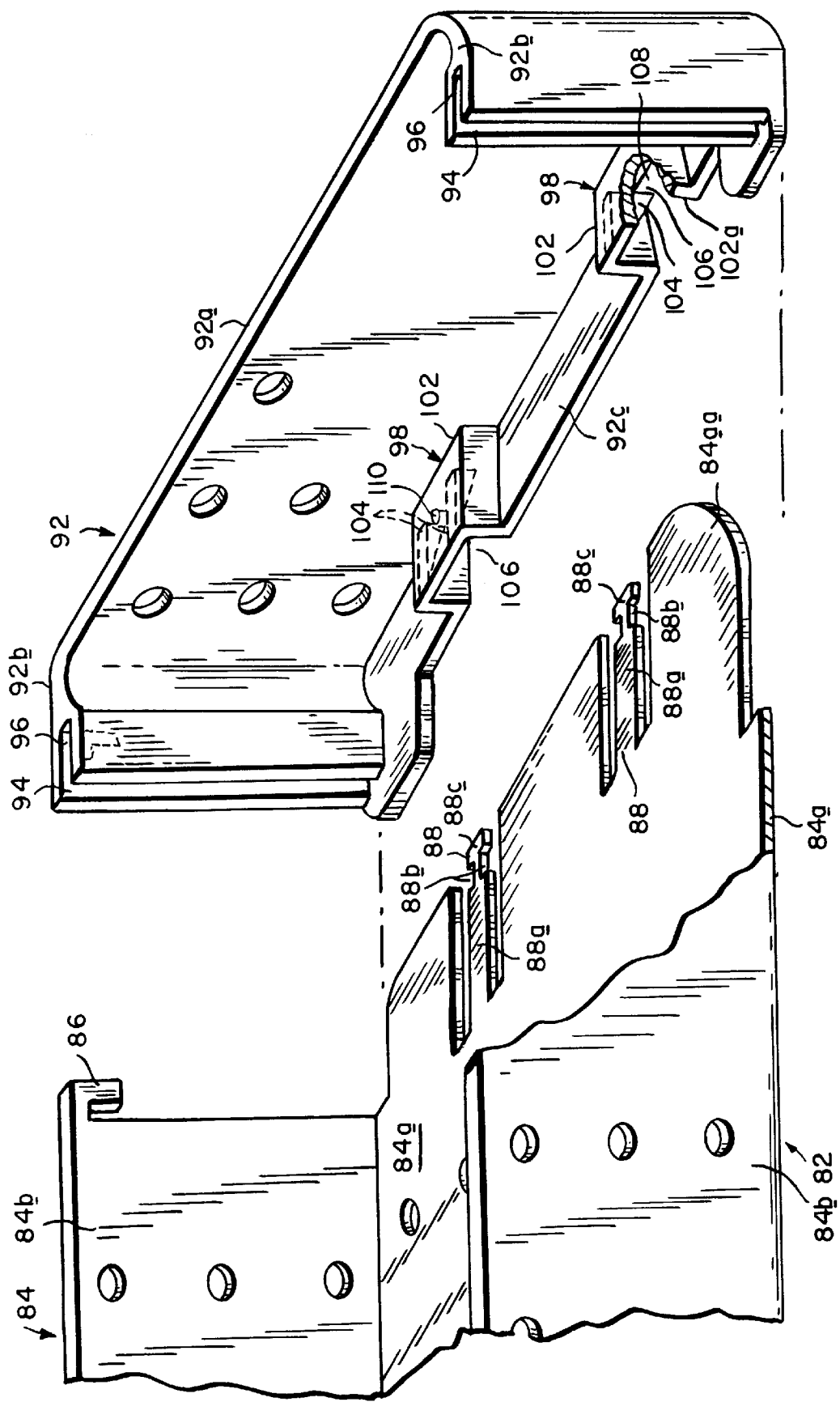
FIG. 6 is a fragmentary exploded perspective view of a third tray embodiment.

Refer now to FIGS. 6, 7A and 7C which illustrate a third embodiment of the sterilization tray which does not require separate fasteners to secure the plastic pieces to the metal portion of the tray. This tray, shown generally at 82, is similar to the FIG. 1 tray in that it has only two plastic pieces which form the end walls of the tray. Tray 82 comprises a perforate metal portion 84 having a bottom wall 84a and a pair of upstanding side walls 84b with hooks 86 at their opposite ends near the upper edges thereof As in the FIG. 1 tray, integral coplanar tongues 84aa extend from the opposite ends of the bottom wall 84a. Each tongue is stamped to form a pair of laterally spaced apart, cantilevered tabs 88. Each tab has an elongated generally rectangular main body 88a, a narrower neck 88b and is terminated by a wider head 88c which extends to the edge of the tongue 84aa. Each tab 88 is resilient so that it can be flexed from the nominal plane of the associated tongue 84aa whereby the tab head 88c lies above or below the tongue.

Tray 82 also includes end closure means in the form of a pair of plastic end walls 92. Each end wall is similar to end wall 22 of the FIG. 1 tray in that it includes a perforate bridging section 92a and a pair of mirror image corner sections 92b at the opposite ends of section 92a. Also, an inwardly extending flange 92c extends along the bottom wall of each end wall 92. As in the end walls 22 of the FIG. 1 tray, a vertical slot 94 and a downwardly facing eye 96 is formed in the end segment of each corner section 92b. The eyes cooperate with the corresponding hooks 86 on the metal portion 84 to attach the end walls to the metal portion in the same way described above in connection with the FIG. 1 tray.

Each end wall 92 is also formed with a pair of laterally spaced apart keepers 98 on its flange 92c. These keepers cooperate with the pair of tabs 88 at the corresponding end of the tray metal portion 84 to secure the lower edge of the end wall to a bottom wall tongue 84aa of the metal portion 84.

Each keeper 98 comprises an inverted, generally U-shaped channel 102 positioned on flange 92c and extending between the edge of that flange and the bridging section 92a. Each channel has a mouth 102a adjacent the flange edge which exposes a pair of laterally spaced apart ramps 104 formed in the top interior wall of the channel. The foot of each ramp lies adjacent to the channel mouth 102a and the head of each ramp is spaced from the wall of bridging section 92a leaving an area 108 inside the channel which is comparable in area to that of the head 88c of each tab 88 on metal portion 84. Furthermore, the gap 106 between the pair of ramps 104 is comparable in shape and dimensions to those of the neck 88b of each tab 88.

Each end wall 92 is assembled to the tray portion 84 in more or less the same way described above in connection with the FIG. 1 tray. More particularly, each end wall 92 is positioned against the corresponding end of tray portion 84 so that the tray portion hooks 86 hook into the eyes 96 at the opposite ends of the end wall. Then the lower edge of the end wall is swung toward the edge of the corresponding tongue 84aa such that the end wall flange 92c engages under that tongue. During the course of this movement, the heads 88c of the tabs 88 on the tray portion 84 will project into the corresponding keepers 98 on that end wall. As best seen in FIG. 7B, the head 88c of each tab 88 encounters the pair of ramps 104 in the corresponding keeper so that continued movement of the end wall toward tray portion 84 causes the tab 88 to be flexed downwardly relative to the remainder of the associated tongue 84aa. However when the end wall is fully seated against the end of tray portion 84, the heads 88c of the two tabs clear the heads of the ramps 104 of the two keepers and the tabs are free to snap back into their unstressed positions wherein each tab head 88c resides in the space 108 in its keeper 98 with the tab neck 88c residing in the gap 106 between the ramps 104 as shown in FIG. 7C.

In this embodiment of the tray, the hooks 86 may have to be tapered somewhat, e.g., about 5°, to provide a certain amount of play when swinging the end wall against tray portion 84 to allow the tabs 88 to be locked into their respective keepers. When fully assembled as shown in FIG. 7C, the end wall 92 is securely fastened to the tray portion 84.

While generally there is no reason to disassemble the tray, provision may be made for doing that. For example, a small hole 110 may be provided in the top wall of each keeper channel 102 directly above space 108 to allow a nail or pin to be forced down into the channel to push the tab head 88c downward sufficiently to clear the heads of the ramps 104 thus releasing associated tab 88 from the keeper. After the lower edge of the end wall 92 is pulled away from the tray portion 84, the upper edge of the end wall can be released from the hooks 86 of that tray portion.

It will thus be seen that the objects set forth above, among those made apparent from the preceding description, are efficiently attained. Also, certain changes may be made in the constructions set forth without departing from the scope of the invention. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A sterilization tray comprising
   a metal main portion having a bottom wall with rounded corners and a pair of mirror-image, spaced apart, parallel side walls extending up from the bottom wall and having corresponding opposite ends;
   a pair of closure means for connecting the corresponding ends of the side walls and the bottom wall to form an enclosure, each closure means including
      a first plastic corner section curved to conform to said rounded corners,
      a second plastic corner section curved to conform to said rounded corners, and
      a bridging section extending between the first and second corner sections;
   first interfitting connection means on one of said side walls and on the first corner section, respectively, for connecting the first corner section to said one side wall and
   second interfitting connection means on the other of said side walls and on said second connection section, respectively, for connecting the second corner section to said other side wall.

2. The tray defined in claim 1 wherein the first interfitting connection means comprise a hook formed on said one of said side walls and an eye formed in the first corner section.

3. The tray defined in claim 2 wherein the second interfitting connection means comprises a hook formed on said other of said side walls and an eye formed in the second corner section.

4. The tray defined in claim 1 wherein the first and second corner sections and the bridging section constitute a unitary part molded of a sterilizable plastic material.

5. The tray defined in claim 1 wherein
   the first corner section is molded of a sterilizable plastic material;
   the second corner section is molded of a sterilizable plastic material;
   the bridging section is a metallic end extension of said main portion bottom wall which extends up from the bottom wall between the first and second corner sections to substantially the same height as the side walls, and further including
   third and fourth interfitting connection means for connecting the end extensions to the first and second corner sections, respectively.

6. The tray defined in claim 5 wherein the third and fourth interfitting connection means each comprise a hook formed on the extension and a second eye formed in each of the first and second corner sections.

7. The tray defined in claim 1 wherein each closure means include a bottom flange that underlies an edge margin of the main portion bottom wall, and fastening means for fastening the flange to the bottom wall.

8. The tray defined in claim 7 wherein the fastening means include one or more rivets extending through the flange and bottom wall.

9. The tray defined in claim 1 wherein each closure means include a bottom flange that underlies an edge margin of the main portion bottom wall;

at least one resilient tab formed in said edge margin, and at least one keeper formed in said flange that receives and retains said tab.

10. The tray defined in claim 9 wherein said tab is cantilevered to said bottom wall, and said keeper includes a ramp that flexes the tab prior to retention of the tab by the keeper.

* * * * *